United States Patent [19]

Frazer et al.

[11] 4,070,113
[45] Jan. 24, 1978

[54] COHERENT OPTICS BLOOD CELL CLASSIFICATION SYSTEM

[75] Inventors: Robert E. Frazer, La Canada, Calif.; Marylou Ingram, Los Alamos, N. Mex.

[73] Assignee: California Institute of Technology, Pasadena, Calif.

[21] Appl. No.: 683,267

[22] Filed: May 5, 1976

[51] Int. Cl.² ............... G01N 21/00; G01N 33/16; H01J 39/12
[52] U.S. Cl. .......................... 356/104; 356/39; 250/211 R
[58] Field of Search ........... 356/102, 103, 104, 39; 250/211 R, 211 J

[56] References Cited

U.S. PATENT DOCUMENTS

| | | | |
|---|---|---|---|
| 3,624,835 | 11/1971 | Wyatt | 356/103 |
| 3,689,772 | 9/1972 | George | 250/211 J |
| 3,777,150 | 12/1973 | Miller | 250/211 R |
| 3,781,112 | 12/1973 | Groner | 356/104 |
| 3,788,744 | 1/1974 | Friedman | 356/39 |
| 3,822,095 | 7/1974 | Hirschfeld | 356/104 |
| 3,910,702 | 10/1975 | Corll | 356/103 |
| 3,928,140 | 12/1975 | Wyatt | 356/104 |
| 3,989,381 | 11/1976 | Fulwyler | 356/39 |

Primary Examiner—Samuel W. Engle
Assistant Examiner—Donald P. Walsh
Attorney, Agent, or Firm—Lindenberg, Freilich, Wasserman, Rosen & Fernandez

[57] ABSTRACT

A system for classifying the various major types of blood cells is provided wherein blood cells are passed before a laser beam. The redirected light energy passing through the cell is applied to a detector array which provides a voltage spectrum representative of the spatial relationships of the object. This voltage spectrum is compared rapidly with different spectra representative of different blood cell classes. Whenever a best fit is detected by the comparing means, a count is scored in one of the cell classes. The same means is applicable to the analysis of other cell types such as cancer and exfoliated cells.

12 Claims, 4 Drawing Figures

COHERENT OPTICS BLOOD CELL CLASSIFICATION SYSTEM

ORIGIN OF THE INVENTION

The invention described herein was made in the performance of work under an NIH Grant RR00443.

BACKGROUND OF THE INVENTION

This invention relates to blood cell classification systems and more particularly to improvements therein.

A system for classifying the various major types of white blood cells in the blood is of urgent need in the area of automated clinical laboratory determinations. In the United States alone, more than a million such determinations are performed in hospital laboratories each day. At present, these are done by relatively unskilled technicians, and studies by the National Center For Disease Control have shown that results are often unreliable. Since this determination, often referred to as a differential white blood cell (WBC) count, is a main stay of clinical laboratory diagnosis, an instrument that would perform it accurately, quickly and at relatively low cost, would represent a significant advance in laboratory medicine. Extensions of the technique to classify exfoliated cervical cells for preliminary indications of cancer would make the instrument even more valuable. Two basic approaches are being taken at present, but as yet an automatic device that provides rapid results with good statistical validity at a cost competitive with those of classification with human technologists does not exist.

The first approach involves comparing a microscope image, using pattern recognition techniques, with the data in the memory of the computer, whereby the various cells within the field of view are inspected. The problem with this approach is its expense and its slow speed. A computer system and peripherals are required and the speed with which the cells can be processed is on the order of that attainable by a human technologist (i.e., 1 per second).

A second approach, and one which is inherently more effective, is one in which cells are introduced on the central line of a tube flowing liquid and are characterized down stream on the basis of size, fluorescent emission, or light absorption measurements, carried out using laser illumination. Classification speed is considerably higher than that attainable with the pattern recognition approach and is on the order of 1,000 cells per second. Little information is drawn from the limited number of measurements to pin point minor differences among white blood cells, and subtleties of classification are realistically traded off with the increased speed and improved statistics.

OBJECTS AND SUMMARY OF THE INVENTION

An object of this invention is to provide a system for automatically classifying white blood cells at a rapid rate.

Another object of this invention is to provide an automatic white blood cell classification system which has a lower cost than presently known systems.

Yet another object of the invention is the provision of a novel and improved cell classification system.

The foregoing and other objects of this invention may be achieved in an arrangement in which a "flow-through" system is employed wherein the specimens are permitted to flow through an optically flat tube, or a central path in a liquid sheath which is illuminated by a laser beam. The output illumination which is scattered at characteristic angles, in passing through the cell, is detected by a detector array having elements at angles of interest. The electric field distribution at the detector plane is the Fourier transform of the object and the intensity distribution is its power spectral density. The power spectrum obtained may be recorded and compared with a library of spectra derived from known particulate matter for a best fit identification.

The detector may comprise a plurality of spaced concentric photovoltaic rings or partial rings. The set of voltages produced by the photovoltaic rings are compared with each of a library of sets of voltages derived from known cells for example, to determine the class into which the cells producing the set of voltages falls. A count of the various cell classes is maintained.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
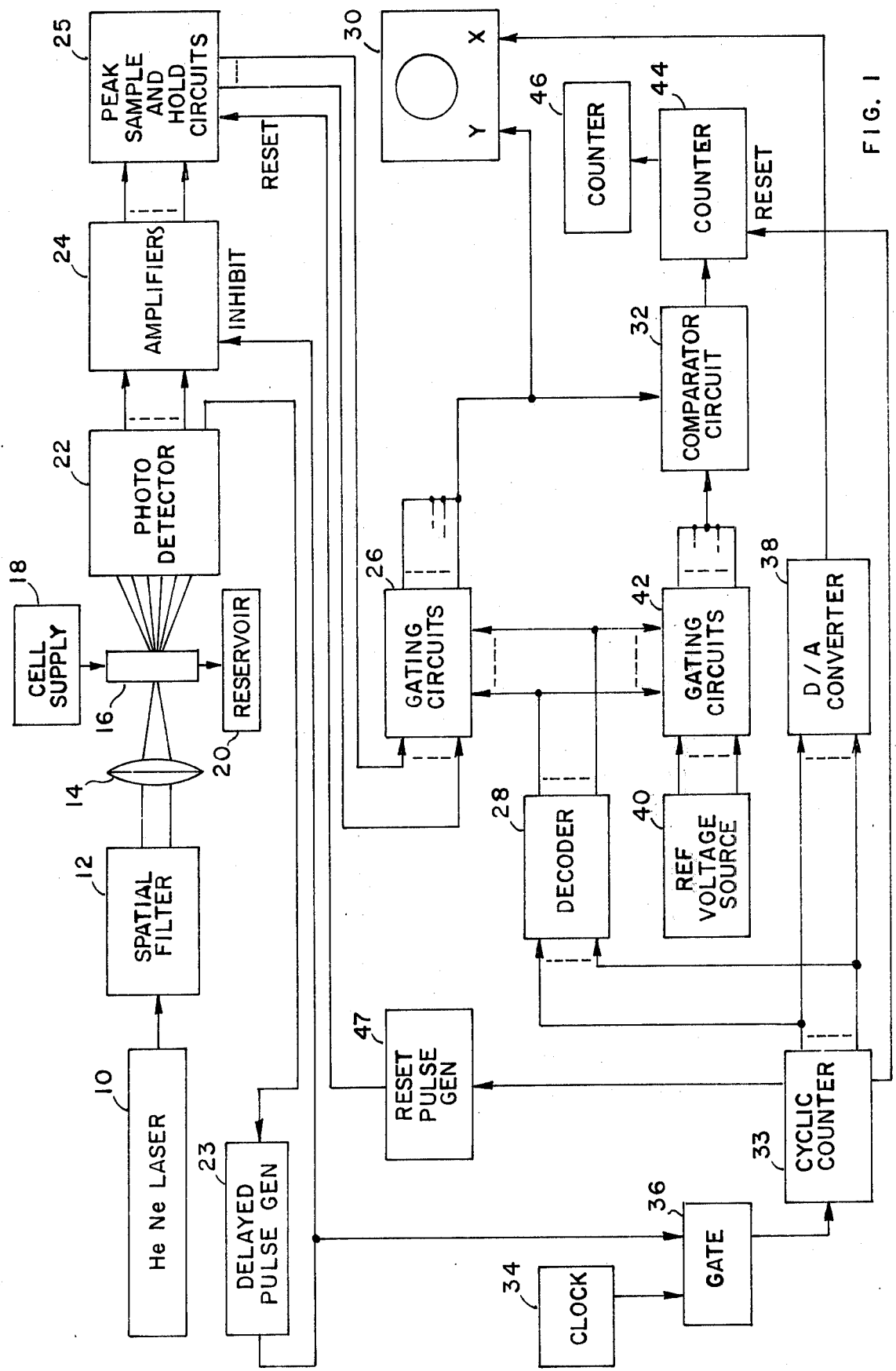
FIG. 1 is a block schematic diagram of an embodiment of the invention.

Referring now to FIG. 1, there is shown a block schematic drawing of an embodiment of the invention. A laser 10, such as helium neon laser, projects its light output at a spatial filter 12. A spatial filter is used to provide a clear, zero order Gaussian beam profile. This permits a smaller spot size to be obtained. The spatial filter is followed by a focusing lens 14 which focuses the light beam on a detector 20. Between the spatial filter and the detector there is positioned a flow-through tube 16, which is a tube with plane parallel walls, or a sheath flow cell, a device well-known in this art. Cells to be inspected are supplied to the flow-through tube from a cell supply 18, and flow therethrough to a catch reservoir 20. In passing through the chamber of the flow-through tube, the cells pass through the area of interest which is illuminated with a uniform optical wavefront of light. The cells disturb this uniform optical waveform and as a result a portion of the incident light is redirected and produces a symmetrical scatter (diffraction) pattern as a Fourier transform of the object. The wavefront disturbance can be caused by a density difference in the cell, or a phase change due to a refractive index variation. Both of these effects are introduced by a typical cell or particle and may vary due to staining or involvement of foreign particles in, or on the cell.

A determination of the scatter parameters generated in the manner described can be accomplished on a stationary object, such as a smear on a slide, or on a moving object such as a cell flowing in a liquid medium through an appropriate windowed test section which is provided by the flow-through apparatus. The Fourier transform process is invarient under translation. Only changes in phase result from position changes. No changes in intensity are observed. This makes the technique usable on cells flowing rapidly through the beam.

Figure 2:
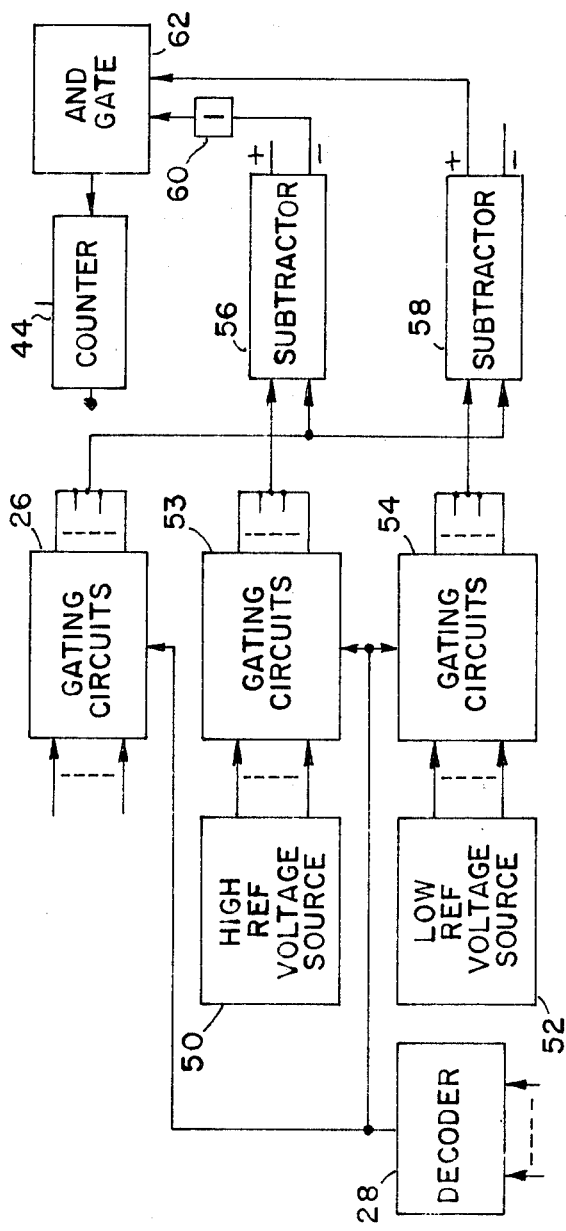
FIG. 2 is a schematic diagram showing a modification of the circuit of FIG. 1.

The scatter pattern generated by the cell passing through the flow-through tube falls on a photodetector 22, which, as shown in FIG. 2 comprises a plurality of concentric photovoltaic ring segments or almost closed rings. By way-of-example, but not by-way-of limitation upon the invention, 16 of those ring segments are used. The scatter pattern falling on these rings accordingly will generate 16 separate output voltages. One or more of the photodetector rings is assigned the task of detecting the presence of a cell. The output from this ring or rings is applied to a delayed pulse generator, which generates a pulse after a short delay. The width of this pulse is determined by the time required for the following circuitry to process the signals derived from the photodetector in response to a cell in the flow-through tube 16.

The output voltages produced by the photodetector 22 are amplified by separate amplifiers, represented by the rectangle labeled "amplifiers 24" and are then applied to separate peak sample and hold circuits 25. The delay time for the output of the delayed pulse generator 23 is sufficient to allow the peak sample and hold circuits to respond to the input from the amplifiers 24. Thereafter, the delayed pulse inhibits the amplifiers preventing them from responding to another cell until the following circuitry has processed the signals in the peak sample and hold circuits. The output of each separate peak sample and hold circuit is applied to a separate gating circuit represented by the rectangle 26. These gating circuits are disenabled, that is they do not pass any of their inputs to their outputs in the absence of a signal from a decoder 28. The decoder output is used to select and enable a different one of the gating circuits at any one time. The number and sequence of selections is determined by the kind of cell or of particulate matter being inspected.

All of the gating circuit outputs are connected together and are applied to the Y deflection terminal input of an oscilloscope 30 and also constitute one input to a comparator circuit 32.

The decoder 28 is driven in response to the output of a cyclic counter 33. A clock pulse source 34 applies pulses to a gate 36. When the gate is enabled it passes these pulses which can then drive the counter 33. The gate 36, is only enabled to apply the clock pulses to the counter in the presence of a pulse from the delayed pulse generator. This occurs when the predetermined one of the photodetector rings senses that a cell or particle is passing through the test section of the laser beam.

The cyclic counter output is also applied to a digital to analog converter 38, which converts the counter outputs to analog signals. These are applied to the X deflection terminal of the oscilloscope 30. As a result, the oscilloscope will display a voltage plot corresponding to the voltage pattern for a cell which is detected by the photodetector 22.

Each different cell, or each different type of particulate matter, will provide a unique spatial pattern which, when applied to the photodetector, causes it to provide a unique set of output voltages. The number of these output voltages which must be inspected or compared with a reference set of voltages to specifically identify a particular cell or voltage pattern varies with the object being inspected. For example, for classifying bone marrow cells, 20 different voltages should be inspected. To classify white blood cells, six different voltages need be inspected. The numbers are different for inspecting exfoliated cells, such as pulmonary washings or cervical vaginal samples or particulate matter which it is desired to inspect for environmental monitoring. Also, the locations of the inspection points over a diffraction pattern, as detected by the photoconductor rings, must be selected, for example, for classifying white blood cells, the six alternate outermost rings typically produce the most significant voltage readings, but this may be a function of detection size, location, light wavelength and cell type.

If the arrangements shown in FIG. 1 is to be used for detecting one particular type of cell or material, then the photodetector need only have the number of properly spaced rings required for that inspection, and the gating circuits will equal those rings in number. A decoder will not be necessary since the gating circuits to which those rings will be connected can be selected to sequence in response to the direct output of a counter. However, in order to enable the apparatus shown in FIG. 1 to accommodate different types of cells, or exfoliated cells, or particulate matter, the photodetector is provided with a plurality of rings. The decoder 28 is one which is either alterable by switches, or may be a changeable "plug in" printed circuit board with a means being provided for enabling the removal of one board and the insertion of another when the type of matter being inspected is altered.

Since a reference voltage pattern is required for each different type of matter being inspected, a reference voltage source 40, which supplies a plurality of reference voltages can also provide an arrangement for changing the amplitudes of the plurality of reference voltages by any of known means.

By way of example, the reference voltage source 40 can comprise a multi-tap resistor connected across a source of reference potential, which resistor is interchangeable, or a plurality of potentiometers, all of which are connected across a common reference source of potential and all of which are individually set so that their outputs provide a desired voltage pattern.

The reference voltages are applied to a second set of gating circuits 42. This constitutes a plurality of disenabled gates, which are enabled in a predetermined sequence by the output of the decoder 28. The enabling sequence will be the same as the one applied to the gating circuit 26. The outputs from all of the gating circuits 40 are connected together and applied, as a second input, to the comparator circuit 32. The first input to the comparator circuit 32 is the output from gating circuits 26.

Each one of the reference voltages from the source 40 is selected by gating circuits 42 in the same sequence as a voltage from the voltage pattern produced by the photodetector is selected. The sequence of voltages from both gating circuits 26 and 42 are compared by the comparator circuit 32. The comparator circuit may be a differential amplifier, or a subtraction circuit, or any other suitable arrangement for comparing two voltages to determine their identicality within a predetermined tolerance range.

Each output of the comparator circuit 32, which occurs upon detecting an acceptable identicality of its inputs, is applied to and actuates a counter 44. Assume that the comparator circuit is supposed to compare 10 voltage parameters to determine or identify a particular type of cell. The comparator circuit will produce 10 outputs indicative of an acceptable comparison of the 10 voltages from the detector and reference voltage source. The counter 44 is advanced to its 10th count by these outputs and its 10th count output is used to advance the count of a second counter 46. The last count state of counter 33 resets counter 44 and thus it is made to assume its starting state in time for the inspection of the next available cell which will pass through the flow-through tube 16. The last count state of counter 33 also enables a reset pulse generator 47, to generate a pulse which is used to reset the peak sample and hold circuits 25.

Counter 33 is driven at a frequency which is high enough so that it completes its count shortly after a cell has passed through the inspection zone of tube 16. The counter 46 will provide a count indicative of the number of the particular cells which have been identified, in the sample being passed through the tube 16.

It should be obvious that the count of counter 44 will be different for each different cell or particulate matter to be identified. Selecting those outputs of the counter 44 to which the input to counter 46 is to be connected is easily accomplished by those skilled in the art.

In order to provide for the situation where for each cell classification a range of reference voltages, or a tolerance range is provided, within which the voltages derived from a cell must fall, FIG. 1 may be modified in the manner shown in FIG. 2. A set of reference voltages, just over the acceptable high side is identified by reference numeral 50. A set of reference voltages just under the low side is identified, by reference numeral 52. The high and low sets of reference voltages are respectively connected to gating circuits 53, 54 which are operated in response to decoder 28 in the same manner as gating circuits 26. The outputs of gating circuits 53 are connected together and applied to the input of a subtractor 56 to be subtracted from the output of gating circuits 26, which is also applied thereto. The outputs of gating circuits 54 are applied to a subtractor 58 and the output of gating circuits 26 is also applied thereto to be subtracted therefrom.

If the voltage outputs from the gating circuits 26 fall within the ranges established by the high reference voltage sources and the low reference voltage sources, then the output from subtractor 56 is negative and the output from subtractor 58 is positive. Subtractor 56 negative output is applied to an inverter 60, to be inverted and applied to an And gate 62. Subtractor 58 positive output is applied to the And gate 60. In the presence of two positive inputs And gate 62 advances the count of counter 44 one count.

A technique for improving the shape stability of cells and thereby the accuracy of this type of inspection is to remove the cytoplasm of the cell by a detergent reaction to allow alignment of the stripped nuclei. When prepared properly, stripped nuclei have remarkable shape stability. Their "water winged" band, spherical, mutlilobed and other distinctive shapes is retained on traversing a flow-through system.

Figure 3:
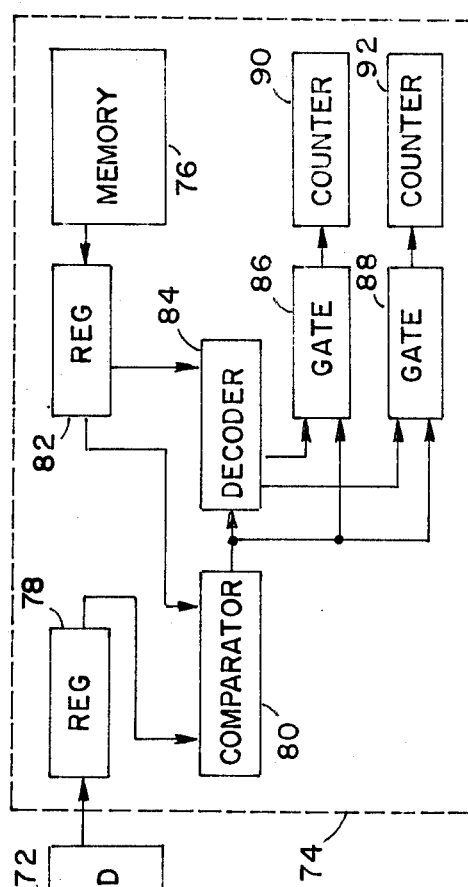
FIG. 3 is a block schematic diagram of an alternative embodiment of the invention.

The system described in FIG. 1 provides an arrangement for detecting one type of cell or particulate matter at a time. Where it is desired to pass a sample of cells in one pass, through the system and to determine what cells are present in the sample and in what a number, a general purpose computer or even a minicomputer may be used. FIG. 3 is a block schematic diagram illustrating such an arrangement. The rectangle labeled "Cell Inspection and Detection" 70 constitutes the laser, spatial filter, flow-through tube arrangement, photodetector amplifiers and peak sample and hold circuits in FIG. 1. The gating circuits 26 are sequentially and directly actuated by the output of counter 33. The gating circuits outputs, comprising the voltages detected by the photodetector are sequentially applied to an A to D converter 72 which applies its digital output to a computer 74.

The computer 74 may be operated either in a real time mode, if fast enough, or in a slower mode. In either event, the computer memory 76 stores a library of patterns of digitized reference voltages, each identifying a cell type, and each appropriately associated with an identifying code. Each successive pattern of digitized voltages supplied to the computer from the A to D converter 72 is placed in a register 78 and then compared by a comparator 80 with all of the patterns successively read into a register 82 from the memory, if the computer is fast enough. Whenever the comparator 80 output indicates an identicality, it produces an output, which enables a decoder 84, to decode the tag associated with the voltage pattern in register 82 at that time. The decoder output is used to enable one of a plurality of gates 86, 88 which can then apply the comparator output to the one of the counters 90, 92, to which it is connected. In this manner a count of the various cell types detected is kept and may be printed out at the end of the run. Where the computer cannot perform the operation in real time then successive patterns of voltages supplied by the A to D converter are first stored and then successively read out of storage and compared with the library of stored reference patterns in the manner described.

The circuit arrangement shown in FIG. 3 may be modified in the manner shown in FIG. 2 to handle tolerance ranges for the cells. That is the memory 76 will provide the high and low reference voltages which are read out into two registers 82. These are applied to two subtractors, as shown in FIG. 2, the outputs from which, when the input received from register 78, is within the range established, will enable a gate whose output actuates the decoder 84 and gates 86 or 88.

The indicated cell or particulate matter identifying technique, using a computer, is a search routine that is readily programmed. The preparation of a library of reference voltage patterns may be readily accomplished by passing known cell or particulate matter types through the feed-through tube, in an arrangement, such as shown in FIG. 2, and tagging and storing the input to the computer.

Figure 4:
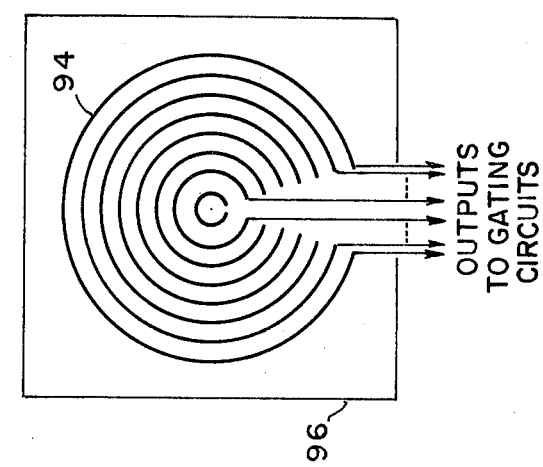
FIG. 4 is a drawing illustrating one type of detector which is employed with the embodiment of the invention.

FIG. 4 is a drawing illustrating a radially symmetric array of photovoltaic elements which comprises a plurality of ring sections 94, made of photovoltaic material, which are formed in or on a substrate 96. Each ring is connected to a different one of the gating circuits 26. The detector array is radially symmetrical, which makes the system insensitive to cell rotation in a plane perpendicular to the axis of the laser. The detector array is to be considered as illustrative and not as limiting.

There has accordingly been described and shown herein a novel and useful system for rapidly inspecting blood samples, or samples of exfoliated cells or, particulate matter for the purpose of identification. The arrangement shown enables one to both visually and automatically determine the particular kind of cell passing through the tube, and also to keep a count of the particular kind of cell.

We claim:

1. A system for identifying particulate matter, such as a cell, comprising means for producing coherent light, flow-through means for passing a supply of particulate matter therethrough, means for focusing light from said coherent light means through said flow-through means to produce a diffraction pattern wherein the light is scattered by particles of said particulate matter at angles characteristic of said matter, means positioned to receive said light scattered at characteristic angles for sensing light scattered at different angles and for producing a set of angle characteristic signal voltages in response thereto, pulse generating means responsive to scattered light for detecting the presence of a scattering particle in said beam and for producing a delayed pulse, peak sample and hold means responsive to said delayed pulse for sampling the peak output voltages of said light sensing means in response to the one scattering particle, wherein each peak output voltage is proportional to the peak intensity of light scattered at a different angle, means establishing a set of reference voltages representative of the characteristic set of peak output voltages produced by particulate matter desired to be identified, and means for comparing the set of characteristic peak output voltages produced by said sample and hold means with the set of reference voltages, and for producing an output when there is an identity between the set of characteristic peak voltages and the set of reference voltages.

2. A system as recited in claim 1 wherein said light sensing means comprises a plurality of spaced concentric partial rings of photovoltaic material, and said means for comparing includes means for comparing the characteristic voltage output produced by each concentric partial ring with a reference voltage.

3. A system as recited in claim 1 wherein said means establishing a set of reference voltages comprises means for establishing a set of reference voltage ranges, and said means for comparing compares the set of characteristic peak voltages with said set of reference voltage ranges.

4. A system as recited in claim 1 wherein there is included means for displaying the set of characteristic peak voltages.

5. A system as recited in claim 1 wherein said light means comprises a plurality of spaced concentric arcs of photovoltaic material, only predetermined ones of which are located to receive the light scattered at angles characteristic of said matter, and said means for comparing includes means for selecting only the peak voltage output from each of said predetermined rings for comparison with said set of reference voltages.

6. A method as recited in claim 1 wherein said means establishing a set of reference voltages comprises means for storing a plurality of reference sets of voltages, and means for sequentially extracting each reference set of voltages from said means for storing for enabling a sequential comparison with a set of characteristic peak voltages.

7. A system for identifying a cell as recited in claim 1 wherein there is included oscilloscope means to which said plurality of characteristic peak voltages are applied for displaying said characteristic voltages as light images.

8. A method of identifying particulate matter, such as a cell, comprising illuminating a particle of said matter with a beam of coherent light to produce a diffraction pattern wherein the light is scattered by said particle at angles characteristic of said matter, generating a set of peak voltages representative of, and in response to, the light scattered at angles characteristic of said matter, establishing a reference set of voltages representative of the light scattered by a particle of known matter, and comparing the set of peak voltages representative of the light scattered at angles characteristic of said matter with said reference set of voltages and producing an output indicative of an identity.

9. A method as recited in claim 8 wherein said step of establishing a reference set of voltages includes establishing a reference set of voltage tolerance ranges, and said set of comparing compares the set of peak voltages with a reference set of voltage tolerance ranges.

10. A method of particle identification as recited in claim 8 wherein said step of generating a set of peak voltages representative of and in response to the light scattered at angles characteristic of a particle of said matter includes placing a plurality of separate photovoltaic materials at locations where they will intercept the light scattered at angles, and deriving a separate peak voltage from each of said plurality of separate photovoltaic materials.

11. A method of cell identification as recited in claim 8 including displaying said plurality of peak voltages representative of the light scattered at characteristic angles.

12. A method for identifying particulate matter as recited in claim 8 wherein said step of establishing a reference set of voltages includes storing a plurality of reference sets of voltages, sequentially establishing from said stored reference sets of voltages each different set of voltages for comparing with said generated set of voltages.

* * * * *

UNITED STATES PATENT AND TRADEMARK OFFICE
CERTIFICATE OF CORRECTION

PATENT NO. : 4,070,113
DATED : January 24, 1978
INVENTOR(S) : Robert E. Frazer & Marylou Ingram It is certified that error appears in the above-identified patent and that said Letters Patent are hereby corrected as shown below:

COLUMN 8 line 3, "A method" should be --A system--

Signed and Sealed this

Eleventh Day of July 1978

[SEAL]

Attest:

RUTH C. MASON
Attesting Officer

DONALD W. BANNER
Commissioner of Patents and Trademarks